United States Patent [19]

Moschitto

[11] Plant 4,852

[45] May 25, 1982

[54] ALMOND TREE

[76] Inventor: Theodore J. Moschitto, 4515 W. Elliot Ave., Merced, Calif. 95340

[21] Appl. No.: 209,992

[22] Filed: Nov. 24, 1980

[51] Int. Cl.[3] ..... A01H 5/03
[52] U.S. Cl. ..... Plt./30
[58] Field of Search ..... Plt./30

*Primary Examiner*—Robert E. Bagwill
*Attorney, Agent, or Firm*—Roger B. Webster

[57] ABSTRACT

An almond tree which is of medium size, open, upright and sturdy, and vigorous; abundantly foliated with large, lanceolate, acutely pointed leaves having a crenate, finely serrate margin and small, alternate, globose glands; blooms heavily with white flowers; and is a regular, mid-season, and very heavy producer of large, well-distributed, light-colored nuts having a relatively thin shell and a medium size, sweet-flavored kernel of good quality.

1 Drawing Figure

BACKGROUND OF THE VARIETY

1. Field of the Discovery

The present new and distinct variety of almond tree is embraced by Class 30, Plants, of the U.S. Pat. Office Manual of Classification.

2. Prior Varieties

Among the existent varieties of almond tree which are known to me, and mentioned herein, are Peerless and Nonpareil (both unpatented).

ORIGIN OF THE VARIETY

The present variety of almond tree was discovered by me growing, as a chance seedling, near my home located in Merced, Merced County, Calif., and—upon recognition by me of its distinctive characteristics, and which are affirmed by subsequent careful and continuing observation—I determined to effect asexual reproduction of the variety with a view toward ultimate commercial growing.

ASEXUAL REPRODUCTION OF THE VARIETY

The present variety of almond tree was asexually reproduced, on my behalf and by a commercial nursery, by scion budding on seedling stock, and such asexual reproductions—in maturity—ran true to the original tree in all respects.

SUMMARY OF THE VARIETY

The herein-claimed variety of almond tree is of medium size, open, upright and sturdy, and vigorous; abundantly foliated with large, lanceolate, acutely pointed leaves having a crenate, finely serrate margin and small, alternate, globose glands; blooms heavily with white flowers; and is a regular, mid-season, and heavy producer of large, well-distributed, light-colored nuts having a relatively thin shell and a medium size, sweet-flavored kernel of good quality.

The herein-claimed variety of almond tree is further characterized as follows:

> The herein-claimed variety of almond tree, while generally similar to the Peerless in appearance, blooms later (as well as later than the Nonpareil) and, therefore, is less subject to frost damage; bears nuts having a thinner shell and hence a higher percentage of kernel to nut; bears nuts whose kernels have a better flavor; and also is a pollenizer for the Nonpareil.

The present variety of almond tree provides, by virtue of its upright and sturdy growth, adequate support for the very heavy crops of nuts regularly borne by the tree.

BRIEF DESCRIPTION OF THE DRAWING

The drawing is an illustration, by photographic reproduction in color, of twigs with leaves and nuts, and, separately, a nut in hull, a nut out of hull, and a kernel.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Density.*—Open.
- *Size.*—Medium.
- *Growth.*—Upright. Sturdy.
- *Vigor.*—Vigorous.

Trunk:
- *Form.*—Stocky.
- *Texture.*—Smooth.

Branches:
- *Form.*—Stocky.
- *Texture.*—Smooth.
- *Lenticels.*—Medium size.
- *Branching habit.*—Medium.
- *Color.*—New wood: Green. Mature wood: Brown.

Foliage:
- *Quantity.*—Abundant.

Leaves:
- *Size.*—Large. Average length — 4.42 inches. Average width — 1.28 inches.
- *Shape.*—Lanceolate. Acutely pointed.
- *Thickness.*—Medium.
- *Texture.*—Smooth.
- *Margin.*—Crenate. Finely serrate.
- *Petiole.*—Length: Medium — average — 1". Thickness: Slender.
- *Glands.*—Average number — 2.86. Alternate. Small. Globose. Green. Positioned on petiole near blade.
- *Stipules.*—None.

*Color.*—Top side — medium glossy green (21-L-7) shading darker. Under side — lighter dull green (21-I-7).

Bloom:

*Amount of bloom.*—Heavy.

*Color of bloom.*—White.

*Blooming period.*—Medium. After Peerless and Nonpareil — about two days after the latter.

Crop:

*Bearing.*—Regular bearer.

*Productivity.*—Very heavy.

*Distribution of nuts on tree.*—Well distributed.

*Harvest period.*—Mid-September. Medium, as compared to other varieties. Two-three days after Nonpareil.

*Tenacity.*—Hangs well on tree. Easy to harvest. Easy to hull.

Hull:

*Outer surface.*—Rough.

*Pits.*—Pitted.

*Form.*—Regular.

*Thickness.*—Thin.

*Flesh.*—Tough.

*Suture.*—Ridged.

*Color.*—Light green (21-J-5) shading to gray-green (15-J-1) with a silvery sheen.

*Dehiscence.*—Opens freely.

*Splitting.*—Along suture. Freely at base.

Nut:

*Size.*—Large. Average length — 33.6 mm. Average width — 20.75 mm. Average thickness — 15.45 mm. Average weight — 2.85 gr.

*Form.*—Length/width: Ovate. Width/thickness: Plump.

*Shell.*—Hard. Thick. Smooth. Outer shell: Hard. Inner shell: Hard. Well sealed.

*Color.*—Light brown (13-L-7) (fresh harvested).

*Pits.*—Large. Numerous. Deep. Round.

*Base.*—Ventrally oblique.

*Stem scar.*—Large. Acute.

*Apex.*—Obtuse. Blunt.

*Wing.*—Narrow. Thin. Tapered toward base.

*Inner surface.*—Medium.

*Ventral streak.*—Narrow. Long. Point obtuse.

*Percentage of kernel to nut.*—39.3%.

Kernel:

*Size.*—Medium. Average length — 23.6 mm. Average width — 12.6 mm. Average thickness — 7.7 mm. Average weight — 25 to an ounce.

*Form.*—Length/width: Elongated. Width/thickness: Medium.

*Base.*—Ventrally oblique.

*Stem scar.*—Large. Acute.

*Apex.*—Obtuse. Blunt.

*Texture.*—Furrowed.

*Pellicle.*—Thick.

*Pubescence.*—Rough. Veined.

*Color.*—Light brown (13-L-9).

*Number of doubles.*—None.

*Defective kernels.*—Few. Deformed kernels — 1%.

*Flavor.*—Sweet.

*Quality.*—Good.

Resistance to insects and diseases: Resistance to insects and fungi the same as Nonpareil.

The almond tree and its nuts herein described may vary in slight detail due to climate and soil conditions under which the variety may be grown; the present description being of the variety as grown in the Central Valley of California.

I claim:

1. A new and distinct variety of almond tree, substantially as illustrated and described, which is upright and sturdy in growth, blooms after the Peerless and Nonpareil, the bloom being heavy and white, and is a regular and very productive bearer of large, light-colored nuts in harvest mid-season; the nuts having a shell thinner than the Peerless, and a sweet kernel of better flavor.

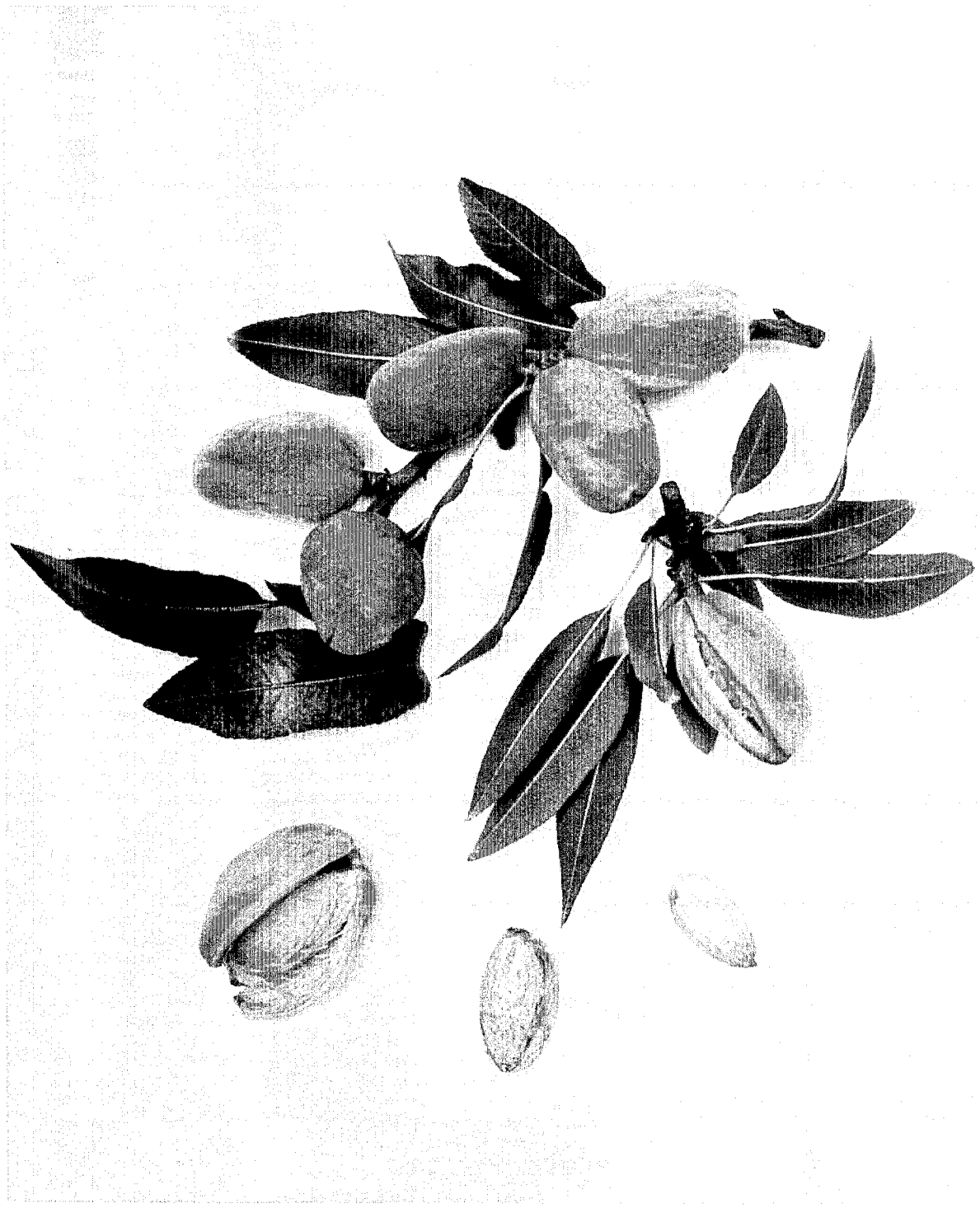

* * * * *